United States Patent
Moussou et al.

(10) Patent No.: US 8,592,484 B2
(45) Date of Patent: Nov. 26, 2013

(54) COSMETIC COMPOSITION CONTAINING CALCIUM CITRATE AND N-ACYLATED AMINOALCOHOL DERIVATIVE TO PREVENT DRY SKIN AND SIGNS OF CUTANEOUS AGEING

(75) Inventors: Philippe Moussou, Tomblaine (FR); Olga Freis, Seichamps (FR); Louis Danoux, Saulxures les Nancy (FR); Philippe Grisoni, Saulxures les Nancy (FR); Laurent Bailly, Essey les Nancy (FR)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/259,632

(22) PCT Filed: Mar. 16, 2010

(86) PCT No.: PCT/EP2010/001644
§ 371 (c)(1),
(2), (4) Date: Sep. 23, 2011

(87) PCT Pub. No.: WO2010/108619
PCT Pub. Date: Sep. 30, 2010

(65) Prior Publication Data
US 2012/0016032 A1   Jan. 19, 2012

(30) Foreign Application Priority Data
Mar. 25, 2009 (EP) ..................................... 09004221

(51) Int. Cl.
*A61Q 19/08*   (2006.01)
*A61K 8/42*   (2006.01)
*A61K 8/365*   (2006.01)

(52) U.S. Cl.
USPC ........... 514/574; 514/625; 514/627; 514/561; 424/78.13

(58) Field of Classification Search
USPC ..................... 514/574, 625, 627; 424/78.13
See application file for complete search history.

(56) References Cited

U.S. PATENT DOCUMENTS

| 2,719,811 | A | 10/1955 | Cook et al. | |
|---|---|---|---|---|
| 5,296,476 | A | 3/1994 | Henderson | |
| 5,851,782 | A | 12/1998 | Hannun et al. | |
| 7,344,868 | B2 * | 3/2008 | Lassalle et al. | 435/129 |
| 2004/0037766 | A1 * | 2/2004 | Kligerman et al. | 423/299 |

FOREIGN PATENT DOCUMENTS

| EP | 588498 | 3/1994 |
|---|---|---|
| EP | 1707211 | 10/2006 |
| JP | 2791179 | 8/1998 |
| WO | WO-02/09687 | 2/2002 |
| WO | WO-2004/017901 | 3/2004 |
| WO | WO-2005/018596 | 3/2005 |
| WO | WO-2005/055927 | 6/2005 |
| WO | WO-2006/000992 | 1/2006 |

OTHER PUBLICATIONS

"Machine Translation of WO02/09687", Mar. 7, 2002, 4 pages.
"PCT International Search Report for PCT/EP2010/001644", Aug. 2, 2010, 5 pages.
Castiel-Higounenc, Isabelle et al., "Stratum Corneum Lipids: Specificity, Role, Deficiencies and Modulation", *Huiles, Corps Gras Et Produits Cosmetiques* 2004, 401-406.
Feingold, Kenneth R., "The Role of Epidermal Lipids in Cutaneous Permeability Barrier Homeostasis", *Journal of Lipid Research*, vol. 48 2007, 2531-2546.
Ghadially, Ruby et al., "The Aged Epidermal Permeability Barrier", *The Journal of Clinical Investigation, Inc.*, vol. 95 May 1995, 2281-2290.
Lochhead, Robert Y. et al., "Encyclopedia of Polymers and Thickeners for Cosmetics. vol. 108", May 1993, 37 pgs.
Ohnish, Yoshinori et al., "Ceramidase Activity in Bacterial Skin Flora as a Possible Cause of Ceramide Deficiency in Atopic Dermatitis", *Clinical and Diagnostic Laboratory Immunology*. vol. 6, No. 1 Jan. 1999, 101-0104.
Sun, Wei et al., "Upregulation of the Human Alkaline Ceramidase 1 and Acid Ceramidase Mediates Calcium-Induced Differentiation of Epidermal Keratinocytes", *The Society for Investigative Dermatology* 2007, 389-397.
Thiele, Jens et al., "Permeability and Antioxidant Barriers in Aged Epidermis", *Chapter 7 in Skin Aging, B. Gilchrest and J. Krutmann Eds, Springer* 2006, 15 pages.

* cited by examiner

*Primary Examiner* — Savitha Rao
(74) *Attorney, Agent, or Firm* — Servilla Whitney LLC

(57) ABSTRACT

Cosmetic compositions comprising calcium citrate and at least one N-acylated aminoalcohol according to formula (I).

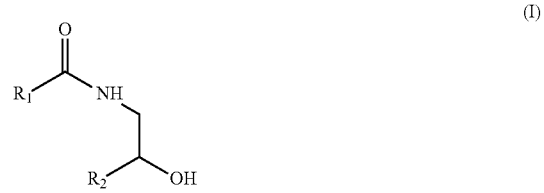

Provided is a method of treating aged skin, comprising topically applying to the aged skin a composition comprising a compound of Formula (I) in an amount effective to provide an anti-ageing effect. The compound of Formula (I) is used to prevent skin and/or to help to maintain or improve moisture retention and/or to fight against the signs of skin ageing. The N-acylated aminoalcohol of formula (I) acts as a ceramidase inhibitor. The combination of at least one compound of formula (I) and calcium citrate stimulates keratinocyte differentiation.

3 Claims, No Drawings

COSMETIC COMPOSITION CONTAINING CALCIUM CITRATE AND N-ACYLATED AMINOALCOHOL DERIVATIVE TO PREVENT DRY SKIN AND SIGNS OF CUTANEOUS AGEING

CROSS-REFERENCE TO RELATED APPLICATIONS

This application is the National Stage entry of PCT/EP2010/001644, filed on Mar. 16, 2010, which claims priority to European Patent application number 09004221.9, filed on Mar. 25, 2009, both of which are incorporated herein by reference in their entireties.

BACKGROUND

1. Field of the Invention

The present invention relates to cosmetic compositions useful for dry and/or sensitive and/or ageing skin.

2. Background Information

Skin is the largest organ of the human body, the condition in which the skin is contributes to a large extent to the well-being of humans. Human skin is exposed to an array of irritants such as UV-light, air pollution etc. In addition extensive sun-bathing or air-conditioning increases the rate of so called dry-skin conditions. In addition there is a trend in modern cosmetics to delay the normal ageing process of human skin, thereby providing a youthful/healthy appearance.

The aim of the invention was to provide a cosmetic composition which can be used on human skin, preferably to prevent dry skin and/or to help to maintain and/or improve moisture retention and/or to fight against the signs of ageing skin. The cosmetic composition should be highly effective, it should be easily applicable in a broad range of cosmetic formulations (e.g. W/O emulsions, O/W emulsions etc.) and it should preferably show little or no irritation on the skin. It has surprisingly been found that the cosmetic compositions according to the invention fulfil these requirements.

WO 2004/017901 describes cosmetic compositions comprising a Ca2+ salt, preferably as Calciumglycerophophate, which can be combined with an alpha-hydroxy acid for skin treatment. U.S. Pat. No. 5,296,476 describes cosmetic compositions comprising micronized calcium citrate in combination with salicylic acid for the treatment of acne. EP 0 588 498 describes calcium citrate in topical compositions for the protection against ultraviolet radiation. WO 2005/018596 describes antiperspirant compositions comprising aluminium-zirconium chlorohydrate antiperspirant salts in combination with a water soluble calcium salt. WO 2005/055927 describes the use of calcium salts for the treatment of acne, warts, rosacea, periodontitis and preventing of scar formation. WO 2006/000992 describes a composition for oral or topical applications, which comprises at least one microorganism in combination with a least on divalent inorganic cation, e.g. calcium citrate. JP 2791179 describes a cosmetic composition with good moisture retention which 1.0-30.0 wt. % at least one selected from a bivalent-trivalent metal salt of acid (e.g. calcium lactate) and a bivalent-trivalent metal hydroxide (e.g. aluminum hydroxide), 3.0-30 wt. % water-soluble salt of alginic acid, 3-20 wt. % oil component and 50-95 wt. powder. Cosmetic compositions comprising Calcium citrate are described in U.S. Pat. No. 2,719,811. The etiology of dry skin is complex, among many other factors skin lipids, such as ceramides are reported to be involved (Castiel-Higounec, M. Chopart, C. Ferraris. Huiles, corps gras et produis cosmétiques, 2004, 11, 401-6]. Topical application of skin lipids has been suggested as remedy (K. R. Feingold. Journal of Lipid Research, 2007, 48, 2531-46). Aged skin is reported to be characterized by altered drug permeability, increased susceptibility to irritant contact dermatitis and severe xerosis (Ghadially et al, 1995 J. Clin. Invest., 1995, 95, 2281-90) Supplying skin with endogenous lipids as well as topically applied anti-oxidants has been suggested to treat aged skin (J Thiele, C. O. Barland, R. Ghadially, P. M. Elias. Permeability and Antioxidant barriers in Aged Epidermis, Chap 7 in Skin Aging, B. Gilchrest and J. Krutmann Eds, Springer, 2006).

The increase of ceramidase in bacterial flora of patients suffering from atopic dermatitis is reported (Y Ohnishi et al. Clinical and Diagnostic Laboratory Immunology 1999, 6, 101-4). U.S. Pat. No. 5,851,782 describes D-erythro-2-(N-myristoylamino)-1-phenyl-1-propanol (D-e-MAPP) as ceramidase inhibitor and its use for the treatment of hyperproliferative diseases/disorders. WO 02/09687 discloses the use of N-Oleylethanolamine for the treatment of psoriasis.

SUMMARY

In accordance with illustrative embodiments and demonstrating features of the present invention, cosmetic compositions are provided for the treatment of aged skin. In one or more embodiments, the compositions comprise calcium citrate and at least one substance according to general Formula (I)

wherein $R_1$ is a linear or branched saturated or unsaturated alkyl moiety with 11 to 17 C atoms, and $R_2$ is selected from the group consisting of —H, —$C_2H_5$, —OH, and —$CH_2OH$. The compositions of the invention treat aged skin by preventing dry skin and/or helping to maintain and/or improve moisture retention and/or maintaining and/or restoring the skin barrier function and/or improving the repair of barrier function of damaged or stressed skin and/or maintaining and/or promoting healthy skin and/or improving the formation of mature cornified envelope and/or enhancing the epidermal differentiation and/or maintaining and/or increasing the levels of epidermal lipids and/or maintaining and/or increasing the level of ceramides in the skin. The compounds of Formula (I) can be used as ceramidase inhibitors, and to boost the effect of calcium salts on epidermal differentiation. In addition, a method is provided for treatment of aged skin, comprising topically applying to the aged skin of a subject in need thereof, a therapeutically effective amount of a compound of Formula (I).

DETAILED DESCRIPTION

The present invention is directed to compositions comprising (a) at least one Calcium salt
(b) at least one ceramidase inhibitor It has surprisingly been found that the compositions of the invention are suitable as cosmetic compositions and/or for the preparation of cosmetic compositions.

A further embodiment of the invention is therefore directed to the use of a composition comprising
(a) at least one Calcium salt
(b) at least one ceramidase inhibitor
in a cosmetic composition and/or for the preparation of a cosmetic composition A preferred embodiment of the invention is directed to the use of
1. Calcium citrate and
2. at least one substance according to formula (I)

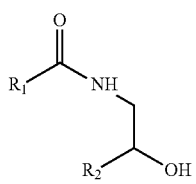

(I)

wherein
$R_1$ is a linear or branched, saturated or unsaturated alkyl moiety with 11 to 17 C atoms
$R_2$ is selected from the group consisting of —H, —CH$_3$, —C$_2$H$_5$, —OH and —CH$_2$OH
in or for the preparation of cosmetic compositions.

In a preferred embodiment, in formula (I), if $R_1$ is —(CH$_2$)$_7$—CH=CH—(CH$_2$)$_7$—CH$_3$ then $R_2$ is not —H.

They are especially suitable in cosmetic compositions
to prevent dry skin and/or
to help to maintain and/or improve moisture retention and/or
to fight against the signs of ageing skin.
to maintain and/or restore the skin barrier function and/or
to improve the repair of barrier function of damaged or stressed skin
to maintain and/or promote healthy skin
to improve the formation of mature cornified envelope
to enhance the epidermal differentiation
to maintain and/or increase the levels of epidermal lipids
to maintain and/or increase the level of ceramides in the skin.

One embodiment of the invention is directed to a method of cosmetically treating skin, hair and/or mucosa, whereby a composition comprising (a) at least one Calcium salt and (b) at least one ceramidase inhibitor is topically applied to skin, hair and/or mucosa.

One embodiment of the invention is directed to a method of cosmetically treating skin, hair and/or mucosa, whereby a composition comprising
a) Calcium citrate and
b) at least one substance according to formula (I)

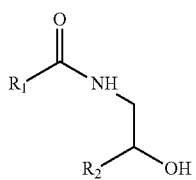

(I)

wherein
$R_1$ is a linear or branched, saturated or unsaturated alkyl moiety with 11 to 17 C atoms
$R_2$ is selected from the group consisting of —H, —CH$_3$, —C$_2$H$_5$, —OH and —CH$_2$OH.
is topically applied to skin, hair and/or mucosa.

In a preferred embodiment, in formula (I), if $R_1$ is —(CH$_2$)$_7$—CH=CH—(CH$_2$)$_7$—CH$_3$ then $R_2$ is not —H.

A further embodiment of the invention is therefore directed to a method of
preventing dry skin and/or
helping to maintain and/or improve moisture retention and/or
fighting against the signs of ageing skin
maintaining and/or restoring the skin barrier function and/or
improving the repair of barrier function of damaged or stressed skin
maintaining and/or promoting healthy skin
improving the formation of mature cornified envelope
enhancing the epidermal differentiation
maintaining and/or increasing the levels of epidermal lipids
whereby a composition comprising
(a) at least one Calcium salt
(b) at least one ceramidase inhibitor
(c) optionally a cosmetically acceptably carrier
is topically applied to skin, hair and/or mucosa.

A further embodiment of the invention is therefore directed to a method of
preventing dry skin and/or
helping to maintain and/or improve moisture retention and/or
fighting against the signs of ageing skin
maintaining and/or restoring the skin barrier function and/or
improving the repair of barrier function of damaged or stressed skin
maintaining and/or promoting healthy skin
improving the formation of mature cornified envelope
enhancing the epidermal differentiation
maintaining and/or increasing the levels of epidermal lipids
whereby a composition comprising
a) Calcium citrate and
b) at least one substance according to formula (I)

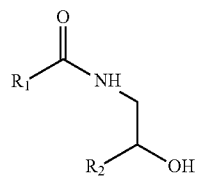

(I)

wherein
$R_1$ is a linear or branched, saturated or unsaturated alkyl moiety with 11 to 17 C atoms
$R_2$ is selected from the group consisting of —H, —CH$_3$, —C$_2$H$_5$, —OH and —CH$_2$OH.
c) optionally a cosmetically acceptably carrier
is topically applied to skin, hair and/or mucosa.

In a preferred embodiment, in formula (I), if $R_1$ is —(CH$_2$)$_7$—CH=CH—(CH$_2$)$_7$—CH$_3$ then $R_2$ is not —H.

Calcium Salt

The Calcium salt present in the cosmetic composition can be any cosmetically acceptable Calcium salt. It is preferably selected from the group consisting of calcium chloride, calcium bromide, calcium nitrate, calcium citrate, calcium formate, calcium acetate, calcium gluconate, calcium ascorbate, calcium lactate, calcium glycinate, calcium aspartate, calcium carbonate, calcium dihydrogen phosphate, calcium glycerophosphate, calcium PCA, calcium phosphate, calcium salicylate, calcium sorbate, calcium sulphate, calcium tartrate, dicalcium phosphate, tricalcium phosphate, calcium hydroxyapatite, calcium behenate, calcium laurate, calcium myristate, calcium propionate, calcium stearate, calcium stearoyl lactylate, calcium undecylenate, and mixtures there of.

In a preferred embodiment of the invention, the Calcium salt is calcium citrate. The term "calcium citrate" is used to encompass the substance tricalcium dicitrate, mostly present as tetrahydrate $[O_2CCH_2C(OH)(CO_2)CH_2CO_2]_2Ca_3.4H_2O]$, molecular weight 570.49. It is commercially available e.g. by Sigma Aldrich (CAS No. 5785-44-4).

The Calcium salt(s) is (are) preferably present in the cosmetic composition in a concentration of 0.0001 and 10 weight-%, preferably between 0.001 and 5 weight-%, more preferably between 0.002 and 2 weight-% based on the final cosmetic composition.

Ceramidase Inhibitor

The ceramidase inhibitor (b) according to the invention is a substance which inhibits the enzyme activity of ceramidase, but does not necessarily act directly on ceramidase to inhibit the activity. The ceramidase inhibitory action of the present invention refers to an action of reducing the activity of ceramidase as compared with the inherent activity of ceramidase, and can be confirmed, for example, according to a method described in EP 1707211B1 [0094]. The inhibitory action on the enzyme activity of ceramidase is not particularly limited as long as the enzyme activity is reduced as compared with the inherent activity of ceramidase, and it is preferable that the activity is inhibited, for example, by 5%, preferably 10%, more preferably 20%, even more preferably 40%, 60%, 80%, and 90%.

Suitable ceramidase inhibitors (b) are substances according to formula (I):

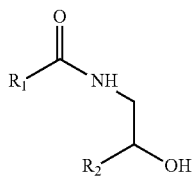

(I)

wherein
$R_1$ is a linear or branched, saturated or unsaturated alkyl moiety with 5 to 21 C atoms
$R_2$ is selected from the group consisting of
—H; —OH; —CH$_2$OH;
—CH$_2$—O—R$_3$, wherein R$_3$ is a C1 to C6 alkyl group
—O—R$_4$, wherein R$_4$ is a C1 to C6 alkyl group and R$_5$, wherein R$_5$ is a C1 to C6 alkyl group Preferred as ceramidase inhibitors according to formula (I) are substances, wherein if $R_1$ is —(CH$_2$)$_7$—CH=CH—(CH$_2$)$_7$—CH$_3$, then $R_2$ is not —H.

$R_1$ is a linear or branched, saturated or unsaturated alkyl moiety with 5 to 21 C atoms, preferably $R_1$ is a linear alkyl moiety; preferably $R_1$ is a saturated alky moiety.

$R_1$ preferably is a saturated or unsaturated alkyl moiety with 7 to 17, preferably 11 to 17 C atoms. Examples of suitable saturated or unsaturated, linear or branched alkyl groups comprising 5 to 21 carbon atoms are n-Pentyl, 1-Methylbutyl-, 2-Methylbutyl-, 3-Methylbutyl, 1-Ethylpropyl, 1,1-Dimethylpropyl, 1,2-Dimethylpropyl, 2,2-Dimethylpropyl, 1-Pentenyl-, 2-Pentenyl-, 3-Pentenyl-, 4-Pentenyl, Hexyl-, 1-Methylpentyl-, 2-Methylpentyl, 3-Methylpentyl, 4-Methylpentyl, 1-Ethylbutyl-, 2-Ethylbutyl-, 3-Ethylbutyl-, 1-Hexenyl, 2-Hexenyl, 3-Hexenyl, 4-Hexenyl-, 5-Hexenyl, Heptyl, 1-Methylhexyl-, 2-Methylhexyl-, 3-Methylhexyl-, 4-Methylhexyl-, 5-Methylhexyl, 1-Hepentyl, 2-Heptenyl, 3-Heptenyl-, 4-Heptenyl-, 5-Heptenyl, 6-Heptenyl-, n-Octyl, 2-Ethylhexyl-,1,1,3,3-Tetramethylbutyl, Nonyl-, Decyl-, Undecyl-, Dodecyl-, Tridecyl-, Tetradecyl-Pentadecyl-, Hexadecyl-, Heptadecyl-, Octadecyl- and Nonadecyl-, —(CH$_2$)$_7$—CH=CH—(CH$_2$)$_7$—CH$_3$, 10-Decenyl, —(CH$_2$)$_7$—CH=CH—CH$_2$—CH=CH—CH$_2$—CH=CH—CH$_2$—CH$_3$, and —(CH$_2$)$_7$—CH=CH—CH$_2$—CH=CH—(CH$_2$)$_4$—CH$_3$.

In a preferred embodiment of the invention a mixture of ceramidase inhibitors according to formula (I) is used, wherein $R_1$ is a mixture of C11 and C13, preferably a mixture of C11, C13 and C15, more preferably a mixture of C11, C13, C15 and C17 moieties.

$R_2$ is selected from the group consisting of —H; —OH; —CH$_2$OH; —CH$_2$—O—R$_3$, wherein R$_3$ is a C1 to C6 alkyl group; —O—R$_4$, wherein R$_4$ is a C1 to C6 alkyl group and R$_5$, wherein R$_5$ is a C1 to C6 alkyl group.

$R_3$, $R_4$ and R5 can be, independent of each other, linear or branched, saturated or unsaturated alkyl groups comprising 1 to 6 C atoms. Examples for are Methyl, Ethyl, Propyl-, iso-Propyl [=1-Methylethyl-], Propenyl-, Isobutyl [2-Methylpropyl], sec-Butyl [=1-Methylpropyl], tert-Butyl [1,1-Dimethylethyl], But-2-enyl, But-3-enyl, But-1-enyl, n-Pentyl, 1-Methylbutyl-, 2-Methylbutyl-, 3-Methylbutyl, 1-Ethylpropyl, 1,1-Dimethylpropyl, 1,2-Dimethylpropyl, 2,2-Dimethylpropyl, 1-Pentenyl-, 2-Pentenyl-, 3-Pentenyl-, 4-Pentenyl, Hexyl-, 1-Methylpentyl-, 2-Methylpentyl, 3-Methylpentyl, 4-Methylpentyl, 1-Ethylbutyl-, 2-Ethylbutyl-, 3-Ethylbutyl-, 1-Hexenyl, 2-Hexenyl, 3-Hexenyl, 4-Hexenyl- and 5-Hexenyl.

In a preferred embodiment $R_2$ is chosen from the group consisting of —H, —OH; —CH$_2$OH and R$_5$, wherein R$_5$ is a C1 to C6 alkyl group, preferably R$_5$ is a C1 to C3 alkyl group.

In a preferred embodiment $R_2$ is chosen from the group consisting of —H, —CH$_3$, —C$_2$H$_5$, —OH and —CH$_2$OH. In a further preferred embodiment $R_2$ is chosen from the group consisting of —H and —CH$_3$.

Further suitable ceramidase inhibitors (b) are selected from the group consisting of D-erythro-2-(N-myristoylamino)-1-phenyl-1-propanol (D-e-MAPP), (1S,2R)-(+)-phenylpropanolamine, (1R,2R)-2-N-myristoylamino-1-(4-nitrophenyl)-1,3-propanediol (D-NMAPPD), N-acyl arginine alkyl ester and/or N-acyl lysine alkyl esters and salts thereof and 22-hydroxy-21-[2-hydroxy-1-(hydroxymethyl)propyl]-3, 26-Hentriacontadienoic acid.

22-hydroxy-21-[2-hydroxy-1-(hydroxymethyl)propyl]-3, 26-Hentriacontadienoic acid is a substance according to (1) which can be used as ceramidase inhibitor:

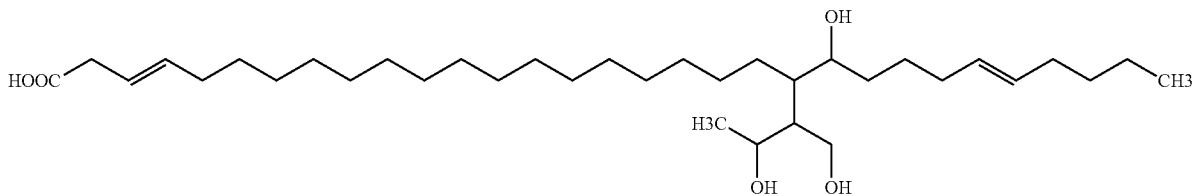
(1)

N-acyl arginine alkyl ester and/or N-acyl lysine alkyl esters are substances according to the following formula:

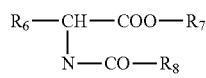

$R_6$=—$(CH_2)_3$—NH—C(=NH)—$NH_2$ (=Arginine) or $R_6$=—$(CH_2)_4$—$NH_2$ (=Lysine)

$R_7$=is a linear or branched, saturated or unsaturated alkyl group comprising 1 to 6 C atoms. For examples of such alkyl groups see alkyl groups exemplified for $R_3$, $R_4$ or $R_5$ above. In a preferred embodiment $R_7$ is methyl or ethyl.

$R_8$=is a linear or branched, saturated or unsaturated alkyl moiety with 7 to 21 C atoms, preferably $R_8$ is a linear alkyl moiety; preferably $R_8$ is a saturated alky moiety. For examples of such alkyl groups see alkyl groups exemplified for $R_1$ above, Examples of such N-acyl arginine alkyl esters and/or N-acyl lysine alkyl esters include N-palm-oil-fatty-acid acyl arginine ethyl ester, N-palm-oil-fatty-acid acyl arginine propyl ester, N-palm-oil-fatty-acid acyl arginine butylester, N-myristoyl arginine ethyl ester, N-myristoyl arginine propyl ester, N-myristoyl arginine butylester, N-palm-oil-fatty-acid acyl lysine ethyl ester, N-palm-oil-fatty-acid acyl lysine propyl ester, N-palm-oil-fatty-acid acyl lysine butylester, Suitable ceramidase inhibitors (b) are furthermore the salts of the N-acyl arginine alkyl ester and/or N-acyl lysine alkyl esters, such as for example, a glycolic acid salt, a pyrrolidone-carboxylic-acid salt, etc. Example of such a salt is the pyrrolidone-carboxylic-acid salt of N-palm-oil-fatty-acid acyl arginine ethyl ester. [N-palm-oil-fatty-acid acyl L-arginic acid ethyl-DL-pyrrolidone-carboxylic-acid salt=N-cocoyl-arginic acid ethyl-DL-pyrrolidone-Carboxylic-acid salt] (Trade name: CAE; INCI name: PCA Ethyl cocoyl arginate) [commercially available from Ajinomoto Co., Inc.].

Further suitable Ceramidase inhibitors (b) are selected from the group consisting of extracts of at least one plant selected from the group consisting of plants belonging to Ginkgoaceae, plants belonging to Cucurbitaceae, plants belonging to Rutaceae, plants belonging to Laminariaceae, plants belonging to Myrtaceae and plants belonging to Compositae.

In a preferred embodiment of the invention it is preferable that, for example, the plant belonging to Ginkgoaceae is ginkgo (*Ginkgo biloba*, Ginkoaceae); the plant belonging to Cucurbitaceae is at least one member selected from the group consisting of Oriental pickling melon (*Cucumis melo* L. var. *conomon* Makino), cucumber (*Cucumis sativus* L.), wax gourd (*Benincasa cerifera* Savi) and bitter cucumber (*Momordica charantia* L.); the plant belonging to Rutaceae is at least one member selected from the group consisting of orange (*Citrus sinensis*, *Citrus aurantium* or *Citrus reticulate*), grapefruit (*Citrus Paradisi*) and lime (*Citrus aurantifolia*); the plant belonging to Laminariaceae is at least one member selected from the group consisting of gagome (*Kjellmaniella crassifolia* Miyabe), kelp (*Laminaria japonica* Areschoug) and wakame seaweed (*Undaria pinnatifida*); the plant belonging to Myrtaceae is eucalyptus; and the plant belonging to Compositae is mugwort (*Artemisia vulgaris* L. var *indica* Maxim.).

The compositions according to the invention can comprise one or more Calcium salts (a) as well as one or more ceramidase innioitors (D).

The Ceramidase inhibitor(s) (b) is (are) preferably present in the cosmetic composition in a concentration of 0.0001 and 10 weight-%, preferably between 0.001 and 5 weight-%, more preferably between 0.002 and 2 weight-% based on the final cosmetic composition. The weight ratio between the Calcium salt(s) (a) and the ceramidase inhibitors(s) (b) is preferably between 50:1 and 1:50, more preferably between 10:1 to 1:10.

It has surprisingly been found that the substances according to formula (I) can be advantageously used as ceramidase inhibitors. A further embodiment of the invention is therefore directed to the use of a substance according to formula (I)

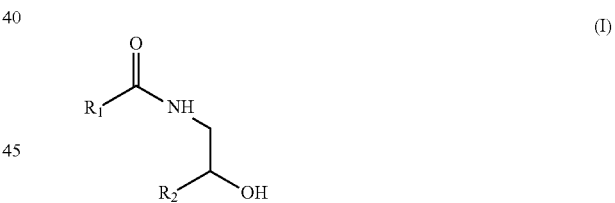
(I)

wherein $R_1$ is a linear or branched, saturated or unsaturated alkyl moiety with 5 to 21 C atoms $R_2$ is selected from the group consisting of
—H; —OH; —$CH_2OH$;
—$CH_2$—O—$R_3$, wherein $R_3$ is a C1 to C6 alkyl group
—O—$R_4$, wherein $R_4$ is a C1 to C6 alkyl group and $R_5$, wherein $R_5$ is a C1 to C6 alkyl group
with the proviso that if $R_1$ is —$(CH_2)_7$—CH=CH—$(CH_2)_7$—$CH_3$ then $R_2$ is not H as ceramidase inhibitor, preferably in cosmetic compositions.

A preferred embodiment of the invention is directed to the use of a substance according to formula (I)

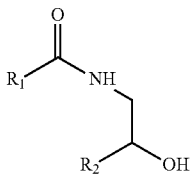

(I)

wherein
$R_1$ is a linear or branched, saturated or unsaturated alkyl moiety with 11 to 17 C atoms
$R_2$ is selected from the group consisting of —H, —CH$_3$, —C$_2$H$_5$, —OH and —CH$_2$OH,
with the proviso that if $R_1$ is —(CH$_2$)$_7$—CH=CH—(CH$_2$)$_7$—CH$_3$ then $R_2$ is not —H,
as ceramidase inhibitor, preferably in cosmetic compositions.

It has furthermore been found that Ceramidase inhibitor(s) are able to increase the effect of Calcium salt(s) on keratinocyte differentiation. A further embodiment of the invention is therefore directed to the use of a ceramidase inhibitor to boost the effect of a calcium salt, preferably calcium citrate, on keratinocyte differentiation. The term "boost" is used to describe an increase in epidermal differentiation of a combination of a Ceramidase inhibitor and a Calcium salt as compared to the epidermal differentiation caused by a Calclium salt alone.

A further embodiment of the invention is directed to the use of a substance according to formula (I)

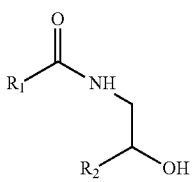

(I)

wherein
$R_1$ is a linear or branched, saturated or unsaturated alkyl moiety with 11 to 17 C atoms
$R_2$ is selected from the group consisting of —H, —CH$_3$, —C$_2$H$_5$, —OH and —CH$_2$OH
to boost the effect of Calcium salts on epidermal differentiation.

A further embodiment of the invention is directed to a cosmetic composition comprising
(a) at least one Calcium salt
(b) at least one substance selected from the group consisting of substances of formula (I)

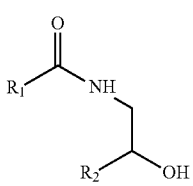

(I)

wherein
$R_1$ is a linear or branched, saturated or unsaturated alkyl moiety with 5 to 21 C atoms $R_2$ is selected from the group consisting of
—H; —OH; —CH$_2$OH;
—CH$_2$—O—R$_3$, wherein R$_3$ is a C1 to C6 alkyl group
—O—R$_4$, wherein R$_4$ is a C1 to C6 alkyl group and R$_5$, wherein R$_5$ is a C1 to C6 alkyl group and/or selected from the group consisting of D-erythro-2-(N-myristoylamino)-1-phenyl-1-propanol (D-e-MAPP), (1S, 2R)-(+)-phenylpropanolamine, (1R,2R)-2-N-myristoylamino-1-(4-nitrophenyl)-1,3-propanediol (D-NMAPPD), and 22-hydroxy-21-[2-hydroxy-1-(hydroxymethyl)propyl]-3,26-Hentriacontadienoic acid, and/or selected from the group consisting of extracts of at least one plant selected from the group consisting of plants belonging to Ginkgoaceae, plants belonging to Cucurbitaceae, plants belonging to Rutaceae, plants belonging to Laminariaceae, plants belonging to Myrtaceae and plants belonging to Compositae.

and/or selected from the group consisting of N-acyl arginine alkyl ester and/or N-acyl lysine alkyl ester and salts thereof, preferably N-coco fatty acyl-L-argininic acid ethyl ester-DL-pyrrolidone carboxylic acid salt.

A preferred embodiment of the invention is directed to a cosmetic composition comprising
a. Calcium citrate and
b. at least one substance according to formula (I)

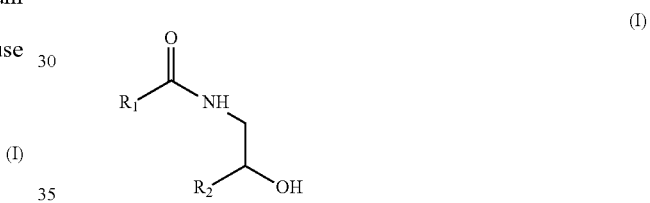

(I)

wherein
$R_1$ is a linear or branched, saturated or unsaturated alkyl moiety with 11 to 17 C atoms
$R_2$ is selected from the group consisting of —H, —CH$_3$, —C$_2$H$_5$, —OH and —CH$_2$OH.

A preferred embodiment of the invention is directed to a cosmetic composition comprising
(a) Calcium citrate and
(b) at least one substance according to formula (I)

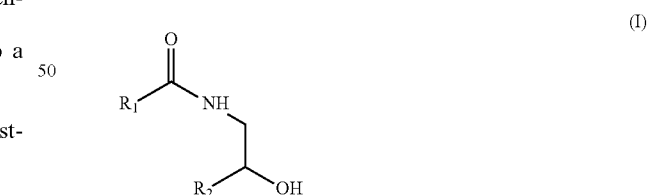

(I)

wherein
$R_1$ is a linear or branched, saturated or unsaturated alkyl moiety with 11 to 17 C atoms
$R_2$ is selected from the group consisting of —H, —CH$_3$, —C$_2$H$_5$, —OH and —CH$_2$OH; with the proviso that if $R_1$ is —(CH$_2$)$_7$—CH=CH—(CH$_2$)$_7$—CH$_3$ then $R_2$ is not —H.

Cosmetic Composition

Cosmetic compositions shall mean any preparation intended to be placed in contact with the various external parts of the human body (epidermis, hair system, nails, lips and external genital organs) or with the teeth and the mucous membranes of the oral cavity with a view exclusively or mainly to cleaning them, perfuming them, changing their appearance and/or correcting body odours and/or protecting them or keeping them in good condition.

The cosmetic compositions according to the invention can for example be in the form of a hair shampoos, hair lotions, foam baths, shower baths, creams, gels, lotions, alcoholic and aqueous/alcoholic solutions, emulsions, wax/fat masses, stick preparations, powders or ointments. These compositions can also comprise, as further auxiliaries and additives, mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, anti-dandruff agents, film formers, swelling agents, insect repellents, self-tanning agents, hydrotropes, solubilizers, preservatives, perfume oils, dyes and the like.

The cosmetic compositions according to the invention can be prepared by adding (a) and (b)—alone or in combination—to the cosmetic composition by means knows to the man skilled in the art.

In one embodiment of the invention the cosmetic composition further comprises at least one surfactant.

Surface-active substances which may be present are anionic, nonionic, cationic and/or amphoteric or zwitterionic surfactants, the content of which in the compositions is usually about 1 to 70% by weight, preferably 5 to 50% by weight and in particular 10 to 30% by weight. Typical examples of anionic surfactants are soaps, alkylbenzenesulphonates, alkanesulphonates, olefinsulphonates, alkyl ether sulphonates, glycerol ether sulphonates, α-methyl ester sulphonates, sulpho fatty acids, alkyl sulphates, alkyl ether sulphates, glycerol ether sulphates, fatty acid ether sulphates, hydroxy mixed ether sulphates, monoglyceride (ether) sulphates, fatty acid amide (ether) sulphates, mono- and dialkyl suiphosuccinates, mono- and dialkyl suiphosuccinamates, sulphotriglycerides, amide soaps, ether carboxylic acids and salts thereof, fatty acid isethionates, fatty acid sarcosinates, fatty acid taurides, N-acylaminoacids, such as, for example, acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants comprise polyglycol ether chains, these can have a conventional homologue distribution, but preferably have a narrowed homologue distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homologue distribution, but preferably have a narrowed homologue distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric and zwitterionic surfactants are alkylbetaines, alkylamidobetaines, aminopropionates, aminoglycinates, imidazoliniumbetaines and sulphobetaines. The specified surfactants are exclusively known compounds.

Typical examples of particularly suitable mild, i.e. particularly skin-compatible, surfactants are fatty alcohol polyglycol ether sulphates, monoglyceride sulphates, mono- and/or dialkyl suiphosuccinates, fatty acid isethionates, fatty acid sarcosinates, fatty acid taurides, fatty acid glutamates, α-olefinsulphonates, ether carboxylic acids, alkyl oligoglucosides, fatty acid glucamides, alkylamidobetaines, amphoacetals and/or protein fatty acid condensates, the latter preferably being based on wheat proteins.

In one embodiment of the invention the cosmetic composition further comprises at least one oil body.

Suitable oil bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols and/or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkyl hydroxy-carboxylic acids with linear or branched $C_6$-$C_{22}$-fatty alcohols in particular dioctyl malates, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, such as, for example, squalane, squalene or dialkylcyclohexanes.

In one embodiment of the invention the cosmetic composition further comprises at least one emulsifier.

Suitable emulsifiers are, for example, nonionogenic surfactants from at least one of the following groups:
　　addition products of from 2 to 30 mol of ethylene oxide and/or 0 to 5 mol of propylene oxide to linear fatty alcohols having 8 to 22 carbon atoms, to fatty acids having 12 to 22 carbon atoms, to alkylphenols having 8 to 15 carbon atoms in the alkyl group, and alkylamines having 8 to 22 carbon atoms in the alkyl radical;

alkyl and/or alkenyl oligoglycosides having 8 to 22 carbon atoms in the alk(en)yl radical and the ethoxylated analogues thereof;

addition products of from 1 to 15 mol of ethylene oxide to castor oil and/or hydrogenated castor oil;

addition products of from 15 to 60 mol of ethylene oxide to castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen grades (TR-1, TR-2) from Goodrich;

polyalkylene glycols, and glycerol carbonate.

Ethylene Oxide Addition Products

The addition products of ethylene oxide and/or of propylene oxide to fatty alcohols, fatty acids, alkylphenols or to castor oil are known, commercially available products. These are homologue mixtures whose average degree of alkoxylation corresponds to the ratio of the amounts of substance of ethylene oxide and/or propylene oxide and substrate with which the addition reaction is carried out. $C_{12/18}$-fatty acid mono- and diesters of addition products of ethylene oxide to glycerol are known as refatting agents for cosmetic preparations.

Alkyl and/or Alkenyl Oligoglycosides

Alkyl and/or alkenyl oligoglycosides, their preparation and their use are known from the prior art. They are prepared, in particular, by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homologue distribution customary for such technical-grade products.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide to said partial glycerides.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxy-stearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of from 1 to 30 mol, preferably 5 to 10 mol, of ethylene oxide to said sorbitan esters.

Polyglycerol Esters

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylgiucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic Emulsifiers

Typical anionic emulsifiers are aliphatic fatty acids having 12 to 22 carbon atoms, such as, for example, palmitic acid, stearic acid or behenic acid, and dicarboxylic acids having 12 to 22 carbon atoms, such as, for example, azelaic acid or sebacic acid.

Amphoteric and Cationic Emulsifiers

Furthermore, zwitterionic surfactants can be used as emulsifiers. The term "zwitterionic surfactants" refers to those surface-active compounds which carry at least one quaternary ammonium group and at least one carboxylate and one sulphonate group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N, N-dimethylammonium glycinates, for example cocoacylaminopropyl-dimethylammonium glycinate, and 2-alkyl-3-carboxymethyl-3- hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds which, apart from a $C_{8/18}$-alkyl or -acyl group, contain at least one free amino group and at least one —COOH or —$SO_3H$ group in the molecule and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, cationic surfactants are also suitable as emulsifiers, those of the ester quat type, preferably methyl-quaternized difatty acid triethanolamine ester salts, being particularly preferred.

In one embodiment of the invention the cosmetic composition further comprises at least one fat or wax.

Typical examples of fats are glycerides, i.e. solid or liquid vegetable or animal products which consist essentially of mixed glycerol esters of higher fatty acids, suitable waxes are inter alia natural waxes, such as, for example, candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithins and phospholipids. The term lecithins is understood by the person skilled in the art as meaning those glycerophospholipids which are founded from fatty acids, glycerol, phosphoric acid and choline by esterification. Lecithins are thus also often as phosphatidylcholines (PC) in the specialist world. Examples of natural lecithins which may be mentioned are the cephalins, which are also referred to as phosphatidic acids and constitute derivatives of 1,2-diacyl-sn-glycerol-3-phosphoric acids. By contrast, phospholipids are usually understood as meaning mono- and preferably diesters of phosphoric acid with glycerol (glycerol phosphates), which are generally classed as fats. In addition, sphingosines or sphingolipids are also suitable.

In one embodiment of the invention the cosmetic composition further comprises at least one pearlescent wax.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

In one embodiment of the invention the cosmetic composition further comprises at least one consistency regulator and/or thickener.

Suitable consistency regulators are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and tyloses, carboxymethylcellulose, hydroxyethylcellulose and hydroxypropylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as, for example, Bentone® Gel VS 5PC (Rheox), which is a mixture of cyclopentasiloxane, disteardimonium hectorite and propylene carbonate, have also proven to be particularly effective. Also suitable are surfactants, such as, for example, ethoxylated fatty acid glycerides, esters of fatty acids with polyols such as, for example, pentaerythritol or trimethylolpropane, fatty alcohol ethoxylates having a narrowed homologue distribution or alkyl oligoglucosides, and electrolytes such as sodium chloride and ammonium chloride.

In one embodiment of the invention the cosmetic composition further comprises at least one superfatting agent.

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

In one embodiment of the invention the cosmetic composition further comprises at least one stabilizer.

Stabilizers which can be used are metal salts of fatty acids, such as, for example, magnesium, aluminium and/or zinc stearate or ricinoleate.

In one embodiment of the invention the cosmetic composition further comprises at least one polymer.

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat®L/Grünau), quaternized wheat polypeptides, polyethyleneimine, cationic silicone polymers, such as, for example, amodimethicones, copolymers of adipic acid and dimethylaminohydroxy-propyldiethylenetriamine (Cartaretins®/Sandoz), copolymers of acrylic acid with dimethyldiallylammonium chloride (Merquat® 550/Chemviron), polyaminopolyamides, and crosslinked water-soluble polymers thereof, cationic chitin derivatives, such as, for example, quaternized chitosan, optionally in microcrystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

In one embodiment of the invention the cosmetic composition further comprises at least one silicone compound.

Suitable silicone compounds are, for example, dimethylpolysiloxanes, methylphenylpolysiloxanes, cyclic silicones, and amino-, fatty acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethyl-siloxane units and hydrogenated silicates.

In one embodiment of the invention the cosmetic composition further comprises at least one UV photoprotective filter.

UV photoprotective factors are, for example, to be understood as meaning organic substances (photoprotective filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:
3-benzylidenecamphor or 3-benzylidenenorcamphor and derivatives thereof, e.g. 3-(4-methylbenzylidene)camphor;
4-aminobenzoic acid derivatives, preferably 2-ethylhexyl 4-(dimethylamino)benzoate, 2-octyl 4-(dimethylamino) benzoate and amyl 4-(dimethylamino)benzoate;
esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenyl-cinnamate (octocrylene);
esters of salicylic acid, preferably 2-ethylhexyl salicylate, 4-isopropylbenzyl salicylate, homomenthyl salicylate;
derivatives of benzophenone, preferably 2-hydroxy-4-methoxybenzophenone, 2-hydroxy-4-methoxy-4'-methylbenzophenone, 2,2'-dihydroxy-4-methoxybenzo-phenone;
esters of benzalmalonic acid, preferably di-2-ethylhexyl 4-methoxybenzalmalonate;
triazine derivatives, such as, for example, 2,4,6-trianilino(p-carbo-2'-ethyl-1'-hexyloxy)-1,3,5-triazine and octyltriazone or dioctylbutamidotriazone (Uvasorb® HEB);
propane-1,3-diones, such as, for example, 1-(4-tert-butylphenyl)-3-(4'-methoxyphenyl)propane-1,3-dione;
ketotricyclo(5.2.1.0)decane derivatives.

Suitable water-soluble substances are:
2-phenylbenzimidazole-5-sulphonic acid and the alkali metal, alkaline earth metal, ammonium, alkylammonium, alkanolammonium and glucammonium salts thereof;
sulphonic acid derivatives of benzophenones, preferably 2-hydroxy-4-methoxybenzophenone-5-sulphonic acid and its salts;
sulphonic acid derivatives of 3-benzylidenecamphor, such as, for example, 4-(2-oxo-3-bornylidenemethyl)benzenesulphonic acid and 2-methyl-5-(2-oxo-3-bornyl-idene)sulphonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds. The UV-A and UV-B filters can of course also be used in mixtures. Particularly favourable combinations consist of the derivatives of benzoylmethane, e.g. 4-tert-butyl-4'-methoxydi-benzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Advantageously, such combinations are combined with water-soluble filters such as, for example, 2-phenylbenzimidazole-5-sulphonic acid and their alkali metal, alkaline earth metal, ammonium, alkylammonium, alkanolammonium and glucammonium salts.

As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminium and cerium, and mixtures thereof. Salts which may be used are silicates (talc), barium sulphate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide.

In one embodiment of the invention the cosmetic composition further comprises at least one biogenic active ingredient and/or antioxidant.

Biogenic active ingredients are understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prunus extract, bambara nut extract and vitamin complexes.

Antioxidants interrupt the photochemical reaction chain which is triggered when UV radiation penetrates the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butyihydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO$_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

In one embodiment of the invention the cosmetic composition further comprises at least one solubilizer. Any known suitable solubilizers can be used, such as e.g. PEG-7-Glycerylcocoate [PEG-7 Glyceryl Cocoate is the polyethylene glycol ether of Glyceryl Cocoate (q.v.) that conforms generally to the following formula, where RCO— represents the fatty acids derived from coconut oil and x+y+z has an average value of 7.

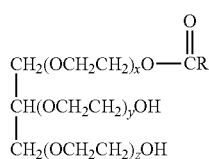

Coceth-7 [Coceth-7 is the polyethylene glycol ether of Coconut Alcohol (q.v.) that conforms to the general formula R—(OCH2CH2)$_n$—OH, wherein R represents the fatty alcohols derived from *Cocos Nucifera* (Coconut) Oil (q.v.) and n has an average value of 7], PPG-1-PEG-9 lauryl glycol ether, PEG-40 hydrogenated castor oil [PEG-40 Hydrogenated Castor Oil is a polyethylene glycol derivative of Hydrogenated Castor Oil (q.v.) with an average of 40 moles of ethylene oxid], PEG-20 glyceryl stearate, [PEG-20 Glyceryl Stearate is the polyethylene glycol ether of Glyceryl Stearate (q.v.) that conforms generally to the following formula, where x+y+z has an average value of 20].

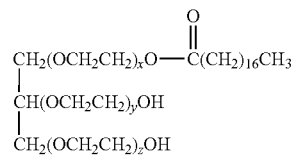

Ceteareth-12 [Ceteareth-12 is the polyethylene glycol ether of Cetearyl Alcohol (q.v.) that conforms generally to the formula R—(OCH$_2$CH$_2$)$_n$—OH wherein R represents a blend of alkyl groups derived from cetyl and stearyl alcohol and n has an average value of 12], Ceteareth-20 [Ceteareth-20 is the polyethylene glycol ether of Cetearyl Alcohol (q.v.) that conforms generally to the formula R—(OCH$_2$CH$_2$)$_n$—OH wherein R represents a blend of alkyl groups derived from cetyl and stearyl alcohol and n has an average value of 20], sodium cetearyl sulphate, or polysorbates (esters of sorbitol and sorbitol anhydrides with long chain fatty acids and condensed with ethylene oxide), such as e.g. Polysorbate-20 (Laurate Esters, approx. 20 moles EO) or Polysorbate-80 (Oleate esters, approx 80 moles EO), or mixtures thereof.

In a preferred embodiment the solubilizer is selected from the group consisting of PEG-7 Glycerylcocoate and/or Ceteareth-20, coceth-7, PPG-1-PEG-9 lauryl glycol ether, PEG-40 hydrogenated castor oil, PEG-20 glyceryl stearate, Ceteareth-12, sodium cetearyl sulphate, and/or polysorbates.

In one embodiment of the invention the cosmetic composition further comprises at least one anti-microbial agent and/or preservative.

Suitable antimicrobial agents are, in principle, all substances effective against gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, N-octylsalicylamide or N-decylsalicylamide.

Suitable preservatives are, for example, phenoxy ethanol, formaldehyde solution, parabens, pentanediol or sorbic acid, and the silver complexes known under the name Surfacins®, and also the other classes of substance listed in Annex 6, Part A and B of the Cosmetics Directive.

In one embodiment of the invention the cosmetic composition further comprises at least one film former.

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

In one embodiment of the invention the cosmetic composition further comprises at least one swelling agent.

The swelling agents for aqueous phases may be montmorillonites, clay mineral substances, Pemulen, and alkyl-modified Carbopol grades (Goodrich). Other suitable polymers and swelling agents are given in the review by R. Lochhead in *Cosm. Toil.* 108, 95 (1993).

In one embodiment of the invention the cosmetic composition further comprises at least one hydrotrophic agent.

To improve the flow behaviour, it is also possible to use hydrotropic agents, such as, for example, ethanol, isopropyl alcohol, or polyols. Polyols which are suitable here preferably have 2 to 15 carbon atoms and at least two hydroxyl groups. The polyols can also contain further functional groups, in particular amino groups, or be modified with nitrogen. Typical examples are glycerol;
alkylene glycols, such as, for example, ethylene glycol, diethylene glycol, propylene glycol, butylene glycol, hexylene glycol, and polyethylene glycols with an average molecular weight of from 100 to 1 000 daltons;
technical-grade oligoglycerol mixtures with a degree of self-condensation of from 1.5 to 10, such as, for example, technical-grade diglycerol mixtures with a diglycerol content of from 40 to 50% by weight;
methylol compounds, such as, in particular, trimethylolethane, trimethylolpropane, trimethylolbutane, pentaerythritol and dipentaerythritol;
lower alkyl glucosides, in particular those having 1 to 8 carbon atoms in the alkyl radical, such as, for example, methyl and butyl glucoside;
sugar alcohols having 5 to 12 carbon atoms, such as, for example, sorbitol or mannitol,
sugars having 5 to 12 carbon atoms, such as, for example, glucose or sucrose;
amino sugars, such as, for example, glucamine;
dialcohol amines, such as diethanolamine or 2-amino-1,3-propanediol.

The total amount of further components can be 1 to 50% by weight, preferably 5 to 40% by weight, based on the compositions. The compositions can be prepared by customary cold or hot processes; preference is given to using the phase-inversion temperature method.

Without intending to limit the invention in any manner, embodiments of the present invention will be more fully described by the following examples.

EXAMPLES

Example 1

N-Oleyl-ethanolamine (CAS 111-58-0) is available from Matreya LLC (Mean MW 325.5). Coconut fatty acid monoisopropanolamide (CAS 68333-82-4) is available from Cognis (Mean MW 279). The C-chain distribution of the fatty acids used is 52-60% C12, 19-23% C14, 8-11% C16, 9-18% C18, thus Coconut fatty acid monoisopropanolamide is a substance according to formula (I) wherein $R_1$ is a mixture of 52-60% C11, 19-23% C13, 8-11% C15, 9-18% C17 alkyl moieties and $R_2$ is —$CH_3$. Coconut fatty acid monoethanolamide (CAS 68140-00-1) is available from Cognis (Mean MW 265). The C-chain distribution of the fatty acid used is 52-60% C12, 19-23% C14, 8-11% C16, 9-18% C18, thus Coconut fatty acid monoethanolamide is a substance according to formula (I) wherein $R_1$ is a mixture of 52-60% C11, 19-23% C13, 8-11% C15, 9-18% C17 alkyl moieties and $R_2$ is —H. Tricalcium citrate tetrahydrate (CAS 5785-44-4) is available from Sigma-Aldrich (MW 570.5).

Example 2

Synthesis of N-lauryl/myristyl-(3-amino-1,2-propanediol) (CAS 92866-80-3 and CAS 35179-73-8)

5 g of a mixture of methyl laurate and methyl myristate (commercially available under the trade name EDENOR®ME C1270 from Cognis GmbH, mean MW 219.2) and 2.08 g of 3-amino-1,2-propanediol (MW 91.1, Sigma-Aldrich) were mixed together at 70° C. After addition of 100 mg of Novozym® 435 (lipase B from Candida Antarctica, from Novozymes), the reaction was conducted during 16 h at 70° C. under moderate agitation and vacuum (250-300 mbars). The mixture was filtrated to remove the immobilized enzyme. The product of the reaction is analyzed by HPLC-DEDL, to give an area ratio of N-lauryl/myristyl-(3-amino-1,2-propanediol)/substrates>98%. Thus N-lauryl/myristyl-(3-amino-1,2-propanediol) is a substance according to formula (I), wherein $R_1$ is a mixture of C11 and C13 alkyl moieties and $R_2$=—$CH_2$—OH Example 3

Synthesis of N-oleyl-(3 amino-1,2-propanediol) (CAS 7336-22-3)

5 g of methyl oleat (commercially available under the trade name EDENOR®ME V05 from Cognis GmbH, MW 296) and 1.54 g of 3-amino-1,2-propanediol (MW 91.1, Sigma-Aldrich) were mixed together at 70° C. After addition of 100 mg of Novozym®435 (lipase B from Candida Antarctica, from Novozymes), the reaction was conducted during 24 h at 70° C. under moderate agitation and vacuum (250-300 mbars). The mixture was filtrated to remove the immobilized enzyme. The product of the reaction was analyzed by HPLC-DEDL, to give an area ratio of N-oleyl-(3 amino-1,2-propanediol)/substrates>83%. Thus N-oleyl-(3 amino-1,2-propanediol) is a substance according to formula (I), wherein $R_1$=—$(CH_2)_7$—CH=CH—$(CH_2)_7$—$CH_3$ and $R_2$=$CH_2$—OH Example 4

Ceramidase Inhibition

Source of Enzyme:

HL60 cells activated with Phorbol 12-myristate 13-acetate (PMA) at 5 nM were cultured in 175 $cm^2$ flasks. After trypsinisation and washings, the cell lysis was performed in a specific buffer (Saccharose 500 mM, EDTA 2 mM, Sodium cholate 4 mg, TritonX-100 1%, Sodium Vanadate 100 mM, PMSF 100 mM, $CaCl_2$ 15 mM, Leupeptine 30 mg/ml, Pepstatine 30 mg/ml, Aprotinine 30 mg/ml). The supernatant obtained after centrifugation constituted the enzymatic extract.

Substrate Preparation and Purification:

The substrate [$^{14}$C]—C16 ceramide (N-palmitoyl-D-Sphingosine) was prepared as follows:

| [$^{14}$C]-C16 ceramide 100 µCi/ml | 8 µCi/ml |
| Triton X-100 0.1% * | 0.046% |
| Sodium cholate 0.2% * | 0.093% |

* in methanol/chloroform (2:1)

Evaporation of the organic phase and dissolution in distilled water. The purification step of the substrate was done by addition of Dole solution (500 µl; Dole solution: isopropanol 40 ml, heptane 10 ml, NaOH 1M 1 ml), heptane (300 µl) and 250 µl of water, followed by centrifugation and recuperation of superior phase. After evaporation and addition of Triton and cholate, the purified substrate was solubilised in distilled water.

Reaction Mixture:

The reaction mixture was incubated at 37° C. during 1 hour. The reaction mixture consisted of 5 µl $MgCl_2$ (50 mM), 25 µl enzymatic extract or buffer; 7.5 µl substrate and 12.5 µl product to be tested. The products to be tested were prepared 4× concentrated in buffer at the tested pH and contained 1% of ethanol in final.

Quantification

The quantification of enzymatic degradation of substrate was realized by measuring of radioactivity in heptane phase. At the end of the enzymatic reaction, 0.5 ml of Dole solution, 0.3 ml heptane and 0.25 ml water was added, the mixture was vortexed and centrifuged at 12 000 g for 5 minutes, the inferior phase was washed twice with 1 ml of heptane, then 0.25 ml H2SO4 0.5 M and 0.5 ml heptane were added. The mixture was vortexed and centrifuged at 12 000 g 5 minutes. The radioactivity was measured in the superior phase by liquid scintillation. Results are expressed as the % of control.

TABLE 1

Ceramidase activity in %/control (mean of an assay in triplicate):

| | Dose (µM) | Ceramidase activity | P |
|---|---|---|---|
| Control | — | 100 | |
| N-Oleyl-ethanolamine | 5 | 98 | Ns |
| | 50 | 94 | Ns |
| | 500 | 79 | $p < 0.01$ |
| Coconut fatty acid monoethanolamide | 5 | 75 | $p < 0.01$ |
| | 50 | 72 | $p < 0.01$ |
| | 500 | 61 | $p < 0.01$ |
| Coconut fatty acid monoisopropanolamide | 5 | 81 | $p < 0.01$ |
| | 50 | 66 | $p < 0.01$ |
| | 500 | 52 | $p < 0.01$ |
| N-lauryl/myristyl-(3-amino-1,2-propanediol) | 5 | 76 | $p < 0.01$ |
| | 50 | 79 | $p < 0.01$ |
| | 500 | 55 | $p < 0.01$ |

TABLE 1-continued

Ceramidase activity in %/control (mean of an assay in triplicate):

| | Dose (µM) | Ceramidase activity | P |
|---|---|---|---|
| N-oleyl-(3 amino-1,2-propanediol) | 5 | 81 | $p < 0.01$ |
| | 50 | 78 | $p < 0.01$ |
| | 500 | 71 | $p < 0.01$ |

Compounds of formula I have significantly inhibited ceramidase activity. At equimolar doses, their inhibition effect was more potent than the inhibition effect of N-Oleyl-ethanolamine.

Example 5

Keratinocyte Differentiation

The purpose was to evaluate the potential of the products to stimulate the differentiation of human keratinocytes into corneocytes and therefore the formation of an optimal skin barrier. The products were tested on primary culture of human keratinocytes by measuring the quantity of synthesized involucrin through an ELISA method. Involucrin is a rod shaped protein of 68 kD released by keratinocytes of early spinous layers up to granular layer of human epidermis.

Human keratinocytes were seeded in growth medium (standard medium MCDB153 completed by Fetal Calf Serum at 2%). After 3-4 days of incubation at 37° C., $CO_2=5\%$, the growth medium was exchanged by standard medium MCDB153 without FCS (untreated control), and with a range of concentrations of products to be tested. After 1 day of incubation at 37° C., $CO_2=5\%$, the lack of cytotoxicity of the different product and doses tested was recorded using MTT test, and the level of involucrin was measured by an ELISA method.

The results are expressed in % versus control and presented as a mean+/−SEM (standard error of mean) of 2 or 3 assays (different donors of keratinocytes) in duplicate or triplicate.

TABLE 2

Rate of involucrin in %/control for $CaCl_2$ and tricalcium dicitrate:

| | $CaCl_2$ | | Tricalcium dicitrate tetrahydrate | |
|---|---|---|---|---|
| | Dose (mM) | Involucrin (in % +/− SEM) | Dose (mM) | Involucrin (in % +/− SEM) |
| Untreated control: MCDB153 | 0 | 0 +/− 3.7 | 0 | 0 +/− 3.7 |
| Ca2+: 0.013 mM | 0.013 | 3.4 +/− 4.6 | 0.0044 | 0.5 +/− 2.6 |
| Ca2+: 0.026 mM | 0.026 | −1.4 +/− 4.6 | 0.0088 | 31.6 +/− 2.9 *** |
| Ca2+: 0.1 mM | 0.1 | 21.9 +/− 5.3 ** | 0.033 | 73.4 +/− 3.7 *** |
| Ca2+ 0.3 mM | 0.3 | 84.4 +/− 1.9 *** | 0.1 | 101.7 +/− 7.2 *** |
| Ca2+: 1 mM | 1 | 100 +/− 7.3 *** | nt | nt |

Student T test:
* $p < 0.05$,
** $p < 0.01$,
*** $p < 0.001$;
nt: not tested

Calcium chloride as well as Tricalcium dicitrate significantly enhance the synthesis of the keratinocyte differentiation marker involucrin (see table 2 above) in a dose-dependent manner. At equimolar doses of Ca2+, the effect of Tricalcium citrate tetrahydrate on keratinocytes differentiation is more potent than the effect of Calcium chloride ($p<0.001$ for concentrations in Ca2+ of 0.026 and 0.1 mM). At these concentrations, Calcium chloride as well as Tricalcium dicitrate has not significantly changed the viability (MTT test) of the human keratinocytes.

TABLE 3

Rate of Involucrin in %/control for coconut fatty acid monoisopropanolamide.

| | Dose (mM) | Dose (% w:v) | Involucrin (in % +/− SEM) |
|---|---|---|---|
| Untreated control: MCDB153 | 0 | — | 0 +/− 3.7 |
| $CaCl_2$: 1 mM | 1 | — | 100 +/− 7.3 |
| Coconut fatty acid monoisopropanolamide | 0.00375 | 0.00010 | 1.9 +/− 1.1 |
| | 0.0075 | 0.00021 | 3.4 +/− 1.5 |
| | 0.015 | 0.00042 | 1.4 +/− 1.7 |

Coconut fatty acid monoisopropanolamide has no effect on the synthesis of the keratinocyte differentiation marker involucrin. At these concentrations, coconut fatty acid monoiso-propanolamide has not significantly diminished the viability (MTT test) of the human keratinocytes.

TABLE 4

Rate of Involucrin in %/control for combination of tricalcium dicitrate and coconut fatty acid isopropanolamide

| | Dose (mM) | Dose (% w/v) | Involucrin (in % +/− SEM) |
|---|---|---|---|
| Untreated control: MCDB 153 | 0 | — | 0 +/− 3.7 |
| 1 mM $CaCl_2$ | 1 | — | 100 +/− 7.3 |
| After treatment with Tricalcium dicitrate tetrahydrate | 0.0044 | 0.00025 | 0.5 +/− 2.6 |
| | 0.0088 | 0.00050 | 31.6 +/− 2.9 *** |
| After treatment with Tricalcium dicitrate tetrahydrate + Coconut fatty acid isopropanolamide | 0.0044 + 0.0179 | 0.00025 + 0.00050 | 14.0 +/− 4.1 * |
| | 0.0088 + 0.0358 | 0.00050 + 0.00100 | 63.9 +/− 6.8 *** |

Student T test:
* p < 0.05,
** p < 0.01,
*** p < 0.001

The combination of tricalcium dicitrate and coconut fatty acid monoisopropanolamide has significantly enhanced the synthesis of the keratinocyte differentiation marker Involucrin. This effect is dose dependent. At these concentrations, the combination has not significantly diminished the viability (MTT test) of the human keratinocytes.

When compared to tricalcium dicitrate alone at the same doses, the, stimulating effect on involucrin synthesis of the combination is more potent (p<0.05 for the lower dose, and p<0.01 for the higher dose), whereas coconut fatty acid monoisopropanolamide alone has no effect. These results demonstrate a synergistic effect of the combination of tricalcium dicitrate and the ceramidase inhibitor coconut fatty acid monoisopropanolamide.

Example 6

Lipids Neosynthesis

The lipids neosynthesis was assessed from the incorporation of [$^{14}$C] acetate in a model of reconstructed epidermis. Reconstructed epidermis at Day 3 were placed in 12-well plates with medium containing the tested compounds (systemic treatment), at the indicated concentrations. Three control epidermis were untreated. [14C] acetate medium (0.75 µCi/wells) was added for all experimental conditions. All treatments were performed in triplicate and the labelling was carried out during a 48-hour incubation period.

After washing epidermis and lysis by treatment with perchloric acid, the lipids were extracted by methanol/chloroform (2:1). The phases were separated by addition of PBS and chloroform and the radioactivity of organic phase was quantified by liquid scintillation after chloroform evaporation to measure total lipids neosynthesis.

TABLE 5

Total lipid neosynthesis after treatment of reconstructed epidermis with the combination of tricalcium dicitrate tetrahydrate 0.002% and coconut fatty acid monoisopropanolamide 0.004%.

| Treatment (% w/v) | Total lipids cpm +/− SEM | % control |
|---|---|---|
| Untreated control | 45 637 +/− 653 | 100 |
| Mixture of tricalcium dicitrate tetrahydrate at 0.002% and coconut fatty acid monoiso-propanolamide at 0.004% | 48 423 +/− 135 | 106 * |

Student T test
* p < 0.05

The addition of combination of tricalcium dicitrate and coconut fatty acid monoisopropanolamide has significantly enhanced the lipid neosynthesis in the reconstructed epidermis.

What is claimed is:

1. A method of treating aged skin, the method comprising topically applying to the aged skin of a subject in need thereof a composition comprising a ceramidase inhibitor compound selected from the group consisting of coconut fatty acid monoethanolamide, coconut fatty acid monoisopropanolamide, N-lauryl/myristyl-(3-amino-1,2-propanediol), and N-oleyl-(3-amino-1,2 propanediol)
   in an amount effective to provide an anti-ageing effect, and
   the composition further comprising calcium citrate.

2. The method of claim 1, wherein the anti-ageing effect is selected from preventing dry skin and/or helping to maintain and/or improve moisture retention and/or maintaining and/or restoring the skin barrier function and/or improving the repair of barrier function of damaged or stressed skin and/or maintaining and/or promoting healthy skin and/or improving the formation of mature cornified envelope and/or enhancing the epidermal differentiation and/or maintaining and/or increasing the levels of epidermal lipids and/or maintaining and/or increasing the level of ceramides in the skin.

3. The method of claim 1, wherein the anti-ageing effect is selected from stimulating the differentiation of human keratinocytes, and stimulating lipid neosynthesis in the epidermis, and combinations thereof.

* * * * *